(12) United States Patent  
Ruettimann

(10) Patent No.: US 8,605,855 B2  
(45) Date of Patent: Dec. 10, 2013

(54) METHOD FOR THE SAMPLE PREPARATION OF LIQUID OR PASTE-LIKE SUBSTANCES FOR MEASUREMENTS WITH X-RAY FLUORESCENCE AND SAMPLE BODIES SUITED THEREFOR

(75) Inventor: Fredy Ruettimann, Mannheim (DE)

(73) Assignee: Terrachem GmbH Analysenlabor, Mannheim (DE)

( * ) Notice: Subject to any disclaimer, the term of this patent is extended or adjusted under 35 U.S.C. 154(b) by 727 days.

(21) Appl. No.: 12/599,687

(22) PCT Filed: May 21, 2008

(86) PCT No.: PCT/EP2008/004061  
§ 371 (c)(1),  
(2), (4) Date: Oct. 14, 2010

(87) PCT Pub. No.: WO2008/141812  
PCT Pub. Date: Nov. 27, 2008

(65) Prior Publication Data  
US 2011/0091012 A1  Apr. 21, 2011

(30) Foreign Application Priority Data

May 21, 2007 (DE) .......................... 10 2007 023 793  
Aug. 17, 2007 (DE) .......................... 10 2007 039 000

(51) Int. Cl.  
*G01N 23/223* (2006.01)

(52) U.S. Cl.  
USPC .......................................................... 378/44

(58) Field of Classification Search  
None  
See application file for complete search history.

(56) References Cited

U.S. PATENT DOCUMENTS

| 4,788,700 A | * | 11/1988 | Kurozumi et al. ............ 378/44 |
| 5,573,585 A |   | 11/1996 | Lauth et al. |
| 6,012,325 A |   | 1/2000  | Ma |

FOREIGN PATENT DOCUMENTS

| DE | 42 07 745 A1 | 9/1993 |
| DE | 43 90 935 C2 | 8/1996 |
| DE | 196 18 773 C1 | 11/1997 |
| DE | 101 21 140 A1 | 7/2002 |
| GB | 1088602 A | 10/1967 |
| JP | 2004 093272 A | 3/2004 |

OTHER PUBLICATIONS

Fontas et al.: "Novel and selective procedure for Cr(VI) determination by X-ray fluorescence analysis after membrane concentration", SPECTROCHIMICA ACTA. Part B: Atomic Spectroscopy, New York, NY, US, vol. 61, No. 4, Apr. 1, 2006, pp. 407-413, XP005515249 ISSN: 0584-8547.

* cited by examiner

*Primary Examiner* — Hoon Song  
*Assistant Examiner* — Danielle Fox  
(74) *Attorney, Agent, or Firm* — Muncy, Geissler, Olds & Lowe, PLLC

(57) ABSTRACT

A process for preparing, and an analysis of, liquid or pasty substances not consisting exclusively of volatile constituents and a sample body for use in such a process. The substance to be analyzed is applied to a rigid sample body with at least one flat and smooth analysis surface formed of an absorptive material. The substance is adsorbed and absorbed by the sample body, and is analyzed using an X-ray fluorescence analysis.

23 Claims, 9 Drawing Sheets

Figure 1A:
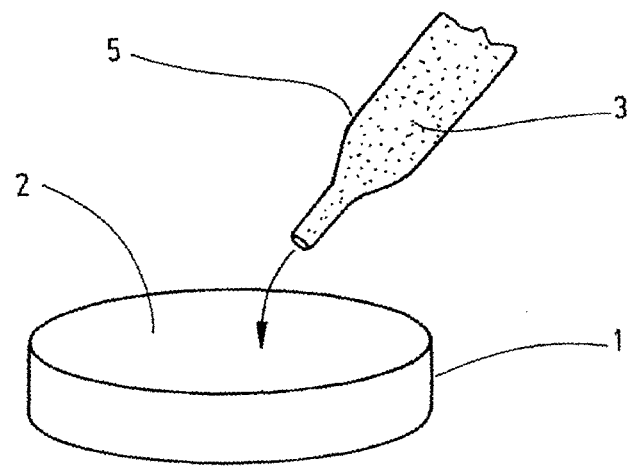

METHOD FOR THE SAMPLE PREPARATION OF LIQUID OR PASTE-LIKE SUBSTANCES FOR MEASUREMENTS WITH X-RAY FLUORESCENCE AND SAMPLE BODIES SUITED THEREFOR

This application is a national stage of International Application No.: PCT/EP2008/004061, which was filed on May 21, 2008, and which claims priority to German Patent Application No.: 10 2007 023 793.8, which was filed in Germany on May 21, 2007, and to German Patent Application No.: 10 2007 039 000.0, which was filed in Germany on Aug. 17, 2007 and which are herein incorporated by reference.

By means of X-ray fluorescence analysis (XFA), it is possible to determine all chemical elements from boron to uranium with very great precision on the basis of their element-characteristic X-radiation. To induce this radiation, high-energy radiation, for example in the form of (primary) X-radiation, has to be directed onto the preparation to be analyzed. This tears electrons out of the inner shells of the elements present therein. As these electron holes are refilled by electrons from outer shells, energy is released, which is emitted as (secondary) X-radiation with an energy or wavelength characteristic of the element in question.

The secondary radiation emitted can be analyzed for the presence of different elements. In the energy-dispersive method (EDXRF), this is done for all elements to be analyzed in one analysis run, in which the energies of the secondary radiation are measured electronically. In the wavelength-dispersive method (WDXRF), the secondary radiation emitted is deflected using an analyzer crystal for each specific element and analyzed quantitatively or qualitatively, such that several analysis runs are required for the determination of more than one element.

Such analyses are used in different fields of elemental analysis. These methods are widespread in geology, the environment and production checks of all kinds. It is possible to determine both main elements and secondary and trace elements. Examples are analyses on glasses, ceramic, oil, fat and the like.

The sample material can be analyzed in the solid or liquid or pasty state. In liquid or pasty substances, the chemical elements to be analyzed may be present either dissolved or suspended in the liquid. A prerequisite for a meaningful analysis is a very homogeneous distribution of the elements to be analyzed within the sample. Solid substances are prepared for the analysis, typically after pulverization, as pressings or fusion products, which are inserted into the analysis apparatus for irradiation and analysis. The analysis operation is effected under vacuum in order to prevent energy losses. Also relevant in this context is the distance between radiation source and substrate for analysis, since radiation losses occur with increasing distance. A smooth surface of the sample body as the analysis surface is therefore required, since very small differences in level can cause analysis inaccuracy.

Liquid and pasty substances are typically introduced into a cuvette, a kind of open plastic cylinder, with the lower orifice sealed with a thin film. These cuvettes are then inserted into the sample carriers of the analysis apparatus like the pressings or fusion products, in which case both the exciting radiation and the generated secondary radiation to be analyzed must penetrate the film. It is therefore a film produced specially for this analysis method. It must be stable enough to hold the liquid on a flat plane. It must also be thin enough to allow sufficient excitation and secondary radiation to pass through.

Since the vacuum which is typically used for the analysis would cause the liquids to be analyzed to boil and exert excessive forces on the film, such samples are analyzed under helium instead of under vacuum. This has the disadvantage that the helium atoms already cause a certain radiation loss. The secondary radiation generated is also additionally impaired by the film, since the secondary radiation of the light elements of the periodic table from boron to fluorine cannot penetrate the film. The "exit depth" of sodium is, for example, 4 µm, and that of the even lighter elements in the periodic table correspondingly lower. A film typically used in XFA has a thickness of 4-6 µm. The analysis of the light elements (in the periodic table) from boron up to and including fluorine is thus impossible with this procedure. For the light elements which follow in the periodic table, sodium and magnesium, such great energy losses still occur that they can be detected only inexactly as trace constituents.

A further disadvantage of the procedure described is that the excitation radiation heats the sample and hence also the film, which has the consequence of expansion and hence "sagging" of the film. The distance thus reduced between radiation source and sample leads to additional analysis inaccuracy. The consequence is that only analyses of the elements from aluminum (No. 13 in the periodic table) are performable reliably to date in X-ray fluorescence analyses of liquid or pasty substances.

Also known is the application of liquid samples to filter material instead, in order to be able to analyze them under vacuum. However, this has the disadvantage that filter material has an inhomogeneous, i.e. rough, surface which also has a tendency to become wavy when liquid is applied and hence leads to analysis inaccuracy. Moreover, such a filter material is unsuitable for several or long-lasting analysis operations because it is damaged by the analysis operation. Thus, long-lasting analysis operations as in the case of the wavelength-dispersive method are impossible.

DE 43 90 935 C2 describes a process for analyzing ambient atmosphere, in which sample bodies composed of metal or ceramic (porous, composed of particles or solid) are exposed to a defined atmosphere over a long period from 24 hours up to 30 days, in order that they sufficiently (physically and/or chemically) bind the atmospheric constituents to be analyzed ($NO_x$, $CO_2$ and $SO_2$). This process is directed exclusively to the analysis of gaseous samples for the constituents measured, and is therefore unsuitable for the analysis of any desired elements, especially not in liquid to pasty substances.

DE 196 18 773 C1 cites further publications and discloses a method for sample preparation of evaporable liquids for XFA on a thin sample carrier material. The evaporated liquids are supplied to the analysis process as a layer on the sample carrier. The coating is achieved by applying a liquid droplet to a very thin, flexible, but tear-resistant and thermally stable polymer film, and drying it by means of a heating apparatus. The process disclosed attempts to solve the problem of achieving a reliable sample geometry during the drying operation. For this method, in the range of the heavy metals, an improved detection limit of less than 10 ppm (instead of 10 ppm to date) and a reduction in the scattered radiation and fluorescence background is reported, though it remains unclear how far the detection limit is actually lowered.

The polymer film described is a tape, as is also known for the production of video and audio tapes. The tape is conducted between two spools, and, after application of the sample by a regulatable pump system, is conducted through a heating apparatus to dry the sample applied. This apparatus comprises a heating table with a preparation plate which has fine holes, to the underside of which a vacuum pump can be attached in order to suck the sample carrier tape onto the preparation plate. The preparation plate also has a structure on the side facing the tape, which serves to emboss a relief for better positioning of the sample into the tape by the action of vacuum during the drying process.

This method has the disadvantage that it is technically complex and is thus expensive to implement. It is also suitable only for readily evaporable liquids. Especially for pasty substances which are difficult to evaporate and tend to form films, for example lubricant oils, this method is not very suitable. There is also, moreover, a limit to the achievable layer thickness of the sample and hence the analysis quality and the lower detection limit. Another contributing factor to this is that a technically complex construction would be required for an analysis under vacuum owing to the use of a continuous sample carrier tape.

It is therefore an object of the invention to provide a process for the sample preparation of liquid to pasty substances, which overcomes the disadvantages of the prior art.

This is achieved by applying the substance to be analyzed to a rigid sample body with at least one flat and smooth analysis surface which consists of absorptive material, the substance being adsorbed and absorbed by this sample body. By definition, the absorptivity of the material here shall equally include the adsorption and absorption operations, no differentiation being made between the physical and chemical level.

This has the advantage that no particular drying apparatus is needed for drying and positioning of the sample, and hence the provision of a reproducible sample with liquid to pasty substances for XFA is likewise possible in a simple manner. It is thus possible to analyze liquid to pasty samples under the same technical conditions as the pressings or fusion products of solid samples, which especially also implies the use of vacuum in the analysis. This allows a homogenous configuration of the analysis apparatus, and a homogeneous way of working in the analysis, irrespective of the consistency of the sample substrates from solid to liquid. A further advantage is that the impregnation of the sample body as a result of the adsorption and absorption of the sample allows a greater irradiatable and analyzable layer thickness to be achieved. As a result, the analysis quality of such samples can be improved significantly: more particularly, the lower detection limit of heavy metals is reduced significantly compared to the prior art (approx. 1 ppm compared to approx. 10 ppm), and the analyzability of the light elements in the periodic table from boron up to and including fluorine is actually made possible at all, and the analysis of sodium and magnesium is performable reliably.

An advantageous configuration of the process envisages using a sample body composed of a material whose absorptivity is such that the substances applied, especially the liquid components, are held within the sample body even under vacuum. This "vacuum-resistant" holding or binding capacity may be based on different alternative or supplementary principles, it being essential that the substance absorbed by suction does not emerge again under vacuum. This property will be discussed further in connection with the inventive sample body. This vacuum-resistant holding or binding capacity has the advantage that such a prepared sample can be subjected to the irradiation and analysis immediately, i.e. without further preparation steps, for example drying.

An advantageous development of the process, especially for the analysis of noncombustible suspended elements, envisages subjecting the sample body to a heat treatment before the analysis, in order to remove the liquid by combustion, especially when it covers the element particles to be analyzed on the analysis surface as an overlying (adsorbed) layer (film). This has the advantage that an exact analysis of noncombustible suspended element particles is possible even in the case of suspensions with pasty liquids of low volatility, for example in the case of metal attritus in lubricant oils.

A prerequisite for such a process is suitable sample bodies which can be employed in this process. The sample bodies must have a rigid consistency in order to provide a stable analysis surface. This analysis surface must, moreover, be flat and especially smooth in order not to impair the analysis result. Moreover, they must be suitable for homogeneously adsorbing and absorbing liquid to pasty substances. It is therefore a further object of the invention to provide a sample body which meets these requirements. This is achieved by virtue of the sample body consisting of an absorptive material. The advantage of such a sample body is that a process of the type described above is enabled with the advantages detailed there.

A particularly advantageous configuration envisages the sample body consisting of a material which can retain or bind liquid to pasty substances sufficiently well that they remain retained and/or bound in the sample body even under vacuum. This "vacuum-resistant" holding and/or binding action can be achieved by a physical and/or chemical route. What is essential is the stability of the holding and/or binding power which endures even a vacuum. The means by which such an action can be achieved include, in addition to the fine structuring of the body and its capillary forces, also the chemical properties of the materials used, such as the capacity to intercalate liquid (intercalation compound) or to bind it in another way. Such an intercalation means is achieved, for example, by using a sample body composed of clay minerals, the material of which has positively and negatively charged chemical structural varieties. Substances whose molecules have an electrical dipole character, for example water, fats, oils and other dipolar liquids, can add onto the correspondingly oppositely charged structural components of the clay mineral with their molecules.

In a feasible configuration, the sample body is a pressing composed of granules. It is thus producible in a simple manner, specifically by pressing in a pre-shaped pressing apparatus. Such a sample body still has a sufficiently smooth surface in the case of correspondingly fine granularity in spite of ultrafine porosity. The granular particles may, in the case of appropriate chemical or mineral properties, particularly efficiently absorb liquid or pasty substances homogeneously in a sufficient amount, once the substance has been sucked into the intestices of the sample body via the surface.

Suitable materials for such granules are, for example, clay minerals or else boehmite. It is essential that they can develop the required absorptivity and a smooth surface. Preference is given to using those materials which also have a "vacuum-resistant" holding or binding action. It is advantageous when they have either no impurities or only minor or at least only defined impurities, in order to prevent distortions of analysis results.

The cited embodiments of the process and of the sample body are merely examples. Further suitable configurations of the process and of the sample body are conceivable.

Figure 1B:
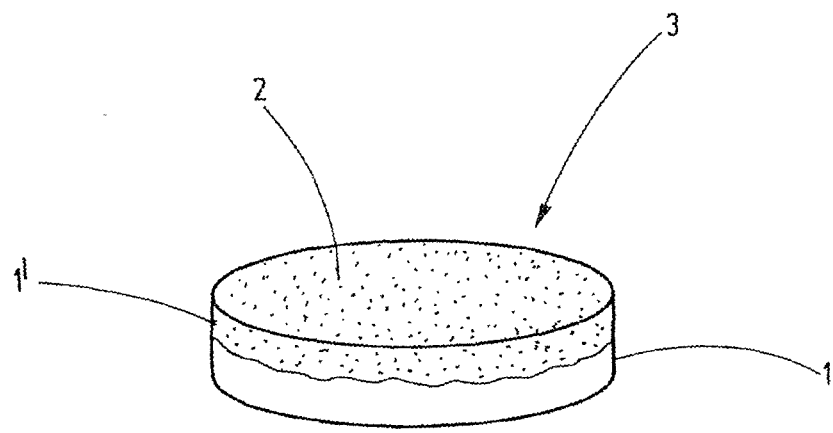
Figure 2A:
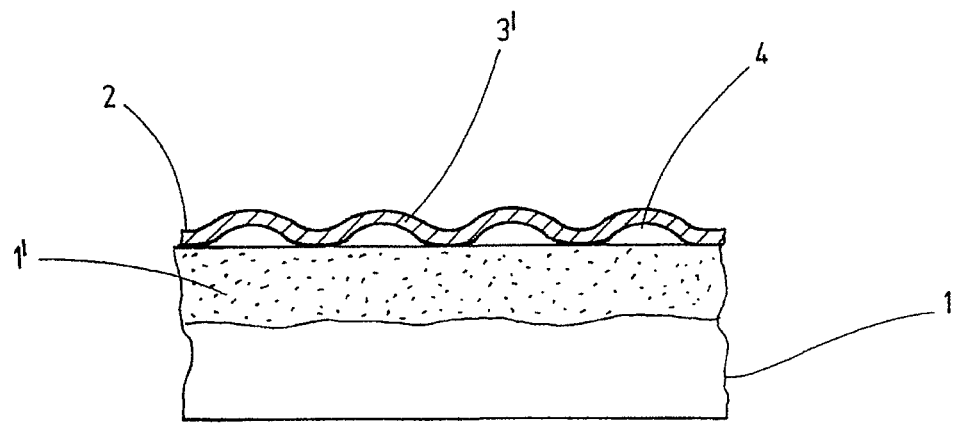
Figure 2B:
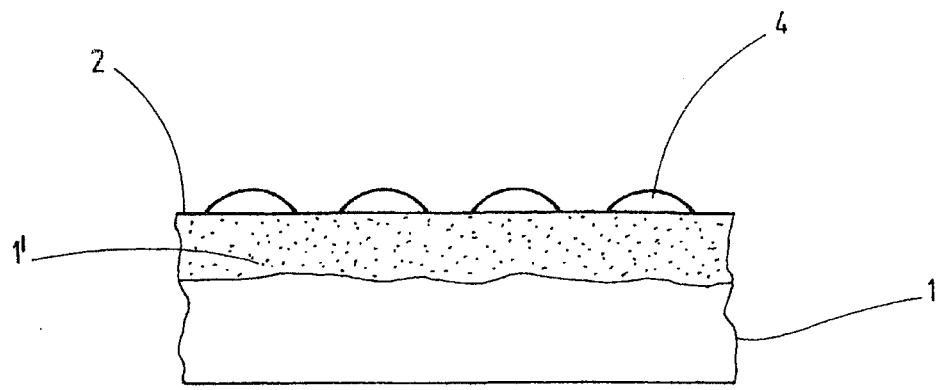

The process and the sample body are illustrated with reference to the drawing. The drawings show:

FIG. 1a application of the liquid or pasty substance to be analyzed to the sample body (step 1 of the process) in schematic view, FIG. 1b a sample body after the adsorption and absorption of the applied substance (step 2 of the process) in schematic view, FIG. 2a a more detailed view of FIG. 1b in section (schematic detail), FIG. 2b the sample body from FIG. 2a after the heat treatment according to claim 3, FIGS. 3 to 9 calibration curves with the illustrative elements boron, magnesium, titanium, manganese, iron, nickel and tin.

FIG. 1a shows the application of the liquid or pasty substance 3 to a sample body 1 (step 1 of the process according to the invention) with a pipette 5. In the example depicted, the sample body 1 has a round shape like the customary pressings or fusion products. However, it may also have any other shapes, as suitable for use in XFA apparatus. The application of the substance with the aid of a pipette 5 is just one illustrative possibility. It will be appreciated that other means of application are also conceivable.

FIG. 1b shows the sample body 1, 1' after adsorption and absorption of the substance 3 into the sample body 1 (step 2) in schematic view, the impregnated region 1' in the example shown comprising only part of the sample body 1 for better illustration. It will be appreciated that the entire sample body 1 may also be impregnated by the substance 3. The elements (dissolved and/or suspended) for analysis which are present in the absorbed substance 3 are not shown. The analysis includes both the elements present in the region of the analysis surface 2 and those which have been sucked into the interior of the sample body. The depth up to which the absorbed elements can be analyzed is connected to the position of the element in the periodic table, i.e. to its intrinsic energy potential. The "heavier" an element is, the more energy such an element can release as a result of the X-radiation, and hence achieve a greater range of the secondary radiation it releases.

FIG. 2a shows a more detailed view of FIG. 1b, i.e. a sample body 1, 1' after application and adsorption and absorption of the substance 3 with suspended element particles 4. Element particles 4 present on the analysis surface 2 have an overlying layer, a film 3'.

FIG. 2b shows, in the same detail as FIG. 2a, a sample body 1, 1' after a heat treatment according to claim 2. The film 3' was combusted by the heat treatment, such that the suspended element particles 4 for analysis are present in free form on the analysis surface 2.

These diagrams are purely schematic; more particularly, the size ratios are not to scale. The required shape of the sample bodies is determined by the analysis apparatus used for the analysis. Round, "tablet-shaped" sample bodies are customary. The desired shaped (and size) is achieved by the shape of the pressing apparatus used. It is essential that there is a smooth analysis surface.

The sample body substrates described and claimed as suitable are merely examples. It will be appreciated that further substances are also very suitable, for example activated carbon, apatite or tricalcium phosphate. These substances mentioned are merely an illustrative selection.

EXAMPLES

FIGS. 3 to 9 show calibration curves for elements selected by way of example. For the analyses by the inventive method, sample bodies composed of boehmite (Al(OH)O) were used, to which 150 mg of the calibration substances were applied for analysis in each case. The sample bodies were produced from 4 g of boehmite in each case as pressings of diameter 40 mm and subjected to the XFA analysis under vacuum. In the tabular representations of the specific analysis values, the following abbreviations and designations are used:
Standard Name Sample Designation
Int. Net. Net intensities measured (peak minus background)
Conc. Chem. Concentrations of the standards used
Conc. XRF Calculated concentrations of the standards on the calibration curve
Abs. Dev. Absolute standard deviation
Re. Dev. Relative standard deviation
LLD (ppm) Lower Level Detection=lower detection limit in ppm (1 ppm=0.0001%)
Kcps Pulse rate of the intensities measured (Kilocounts per second)

Figure 3:
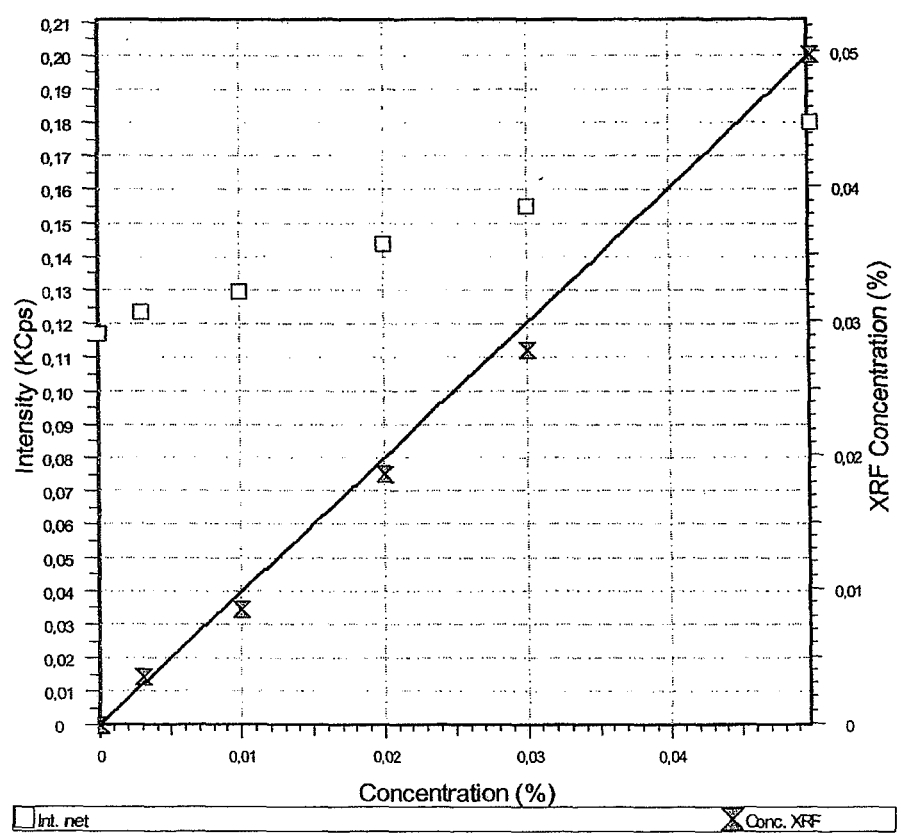
Figure 4:
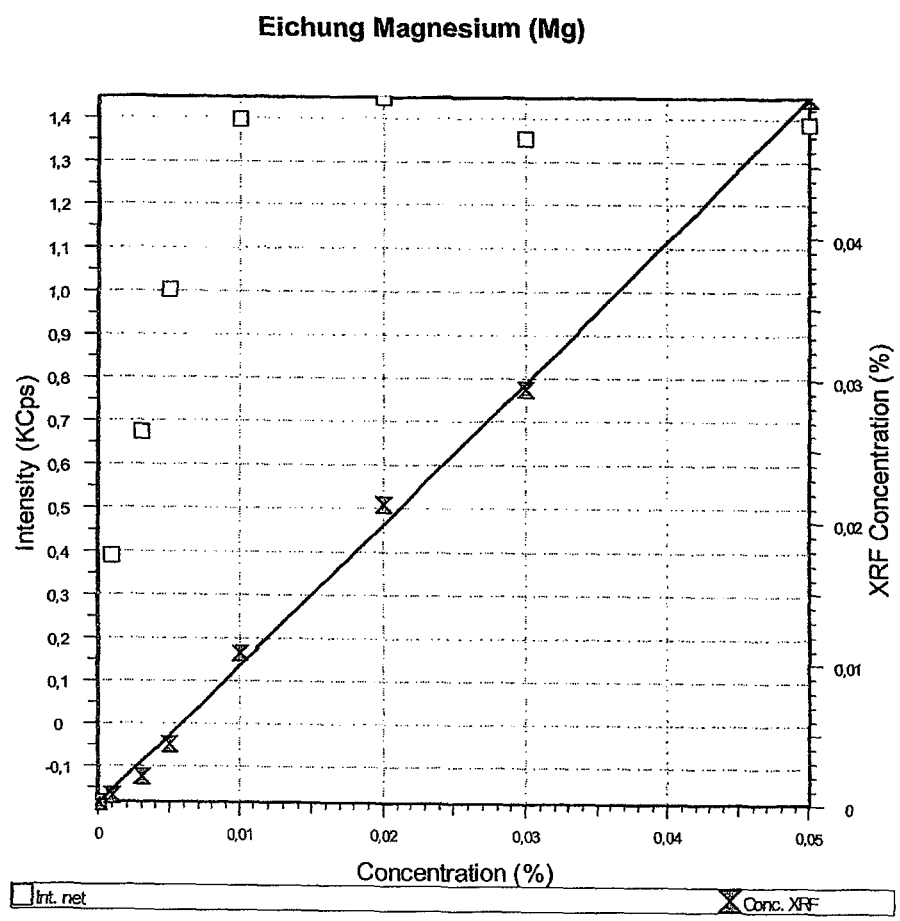
Figure 5:
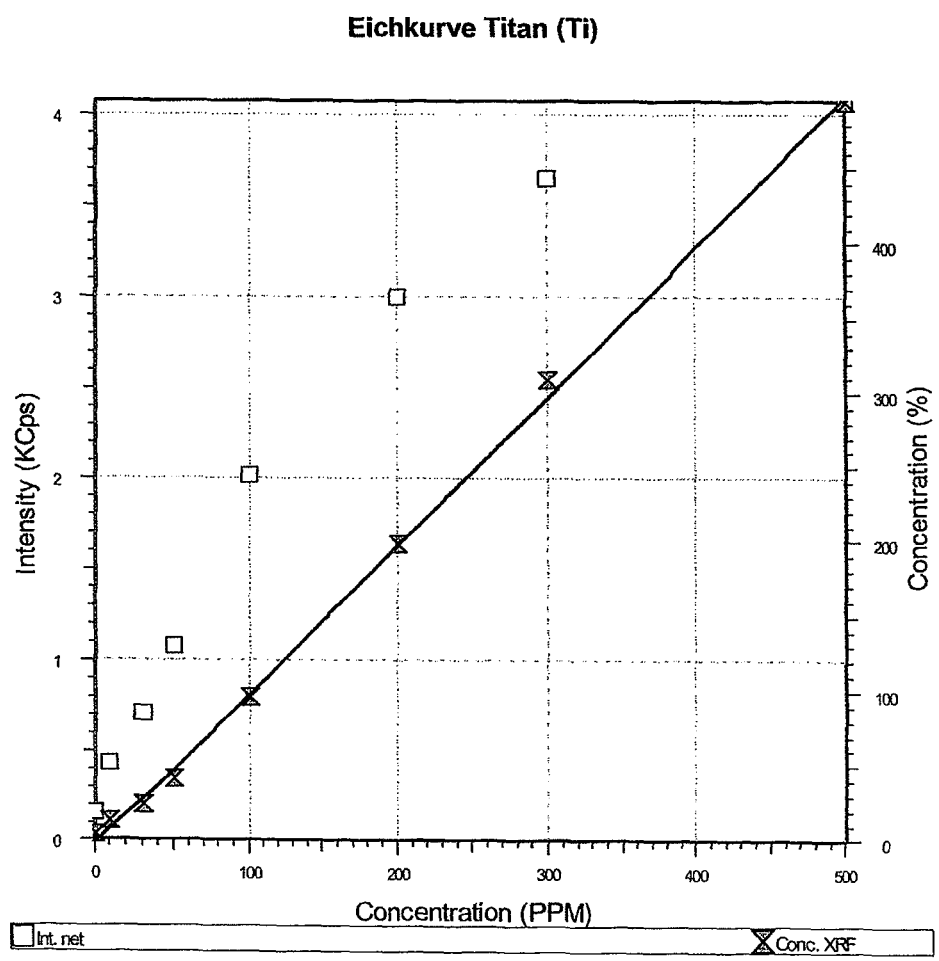
Figure 6:
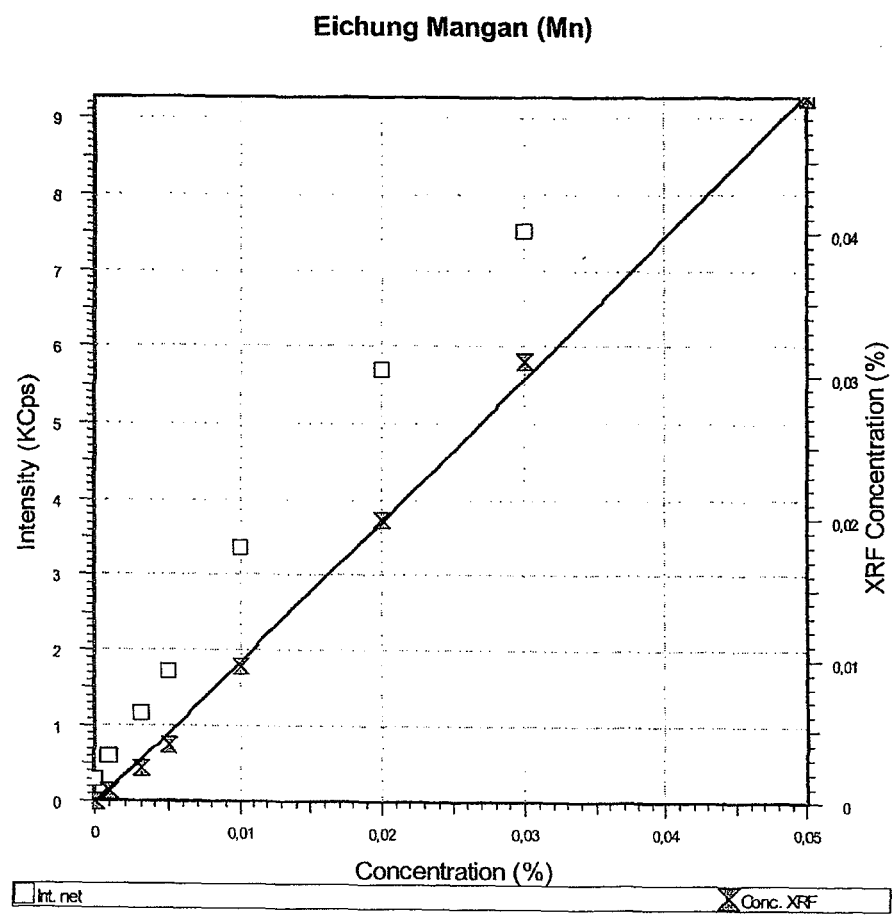
Figure 7:
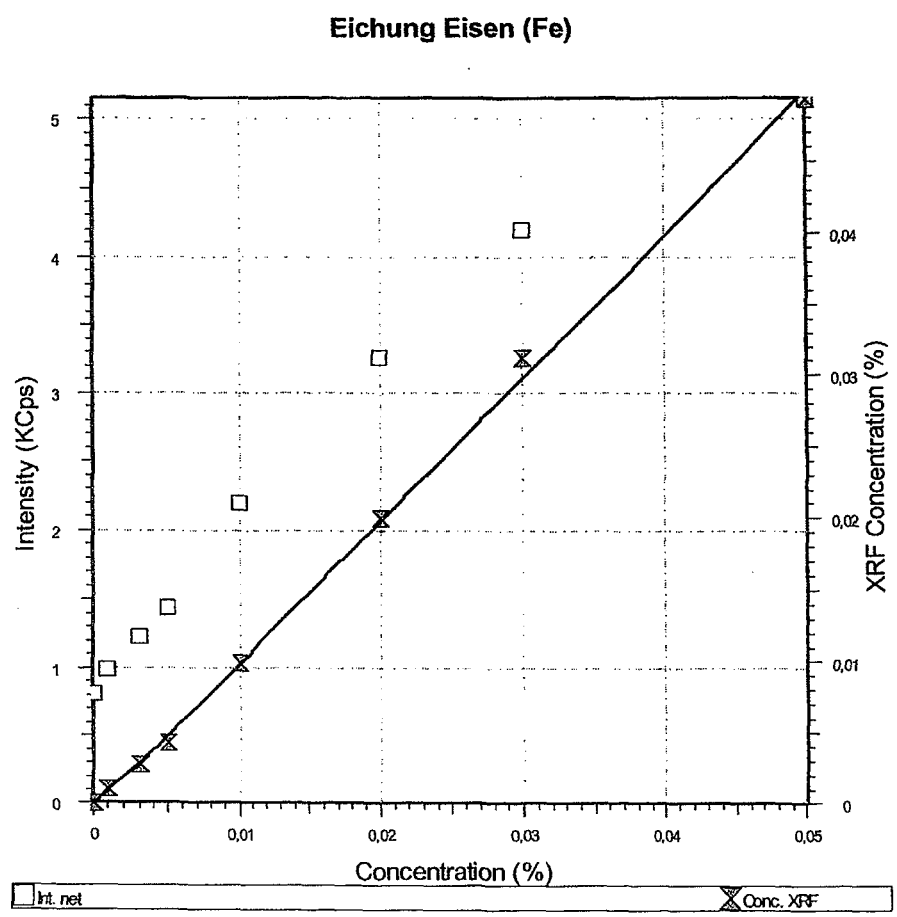
Figure 8:
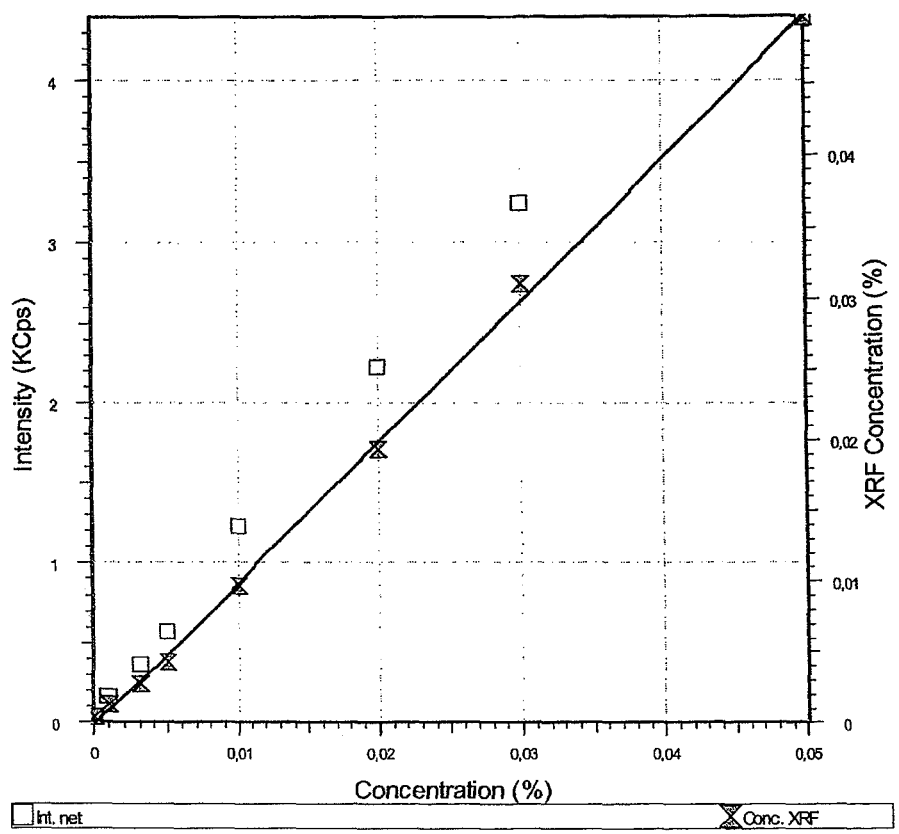
Figure 9:
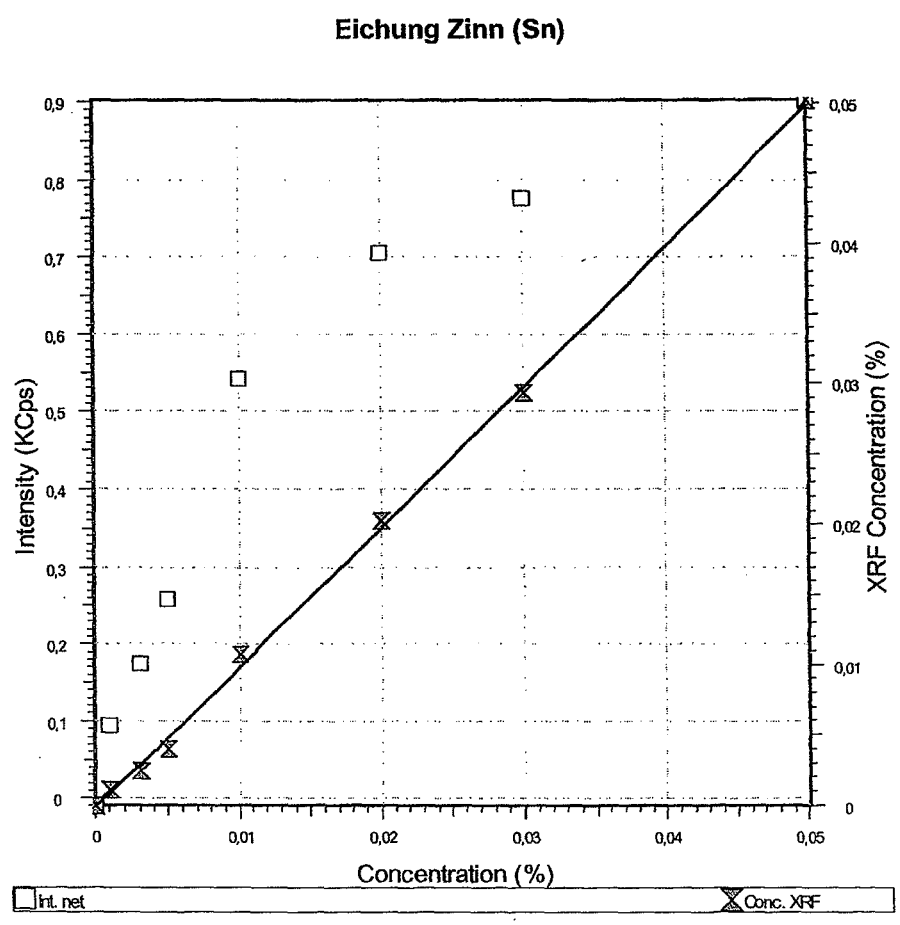

FIGS. 3 and 4 show calibration curves for the light elements boron (B) and magnesium (Mg), for which XFA analyses by conventional processes were not possible at all (boron) or were only possible with great difficulty (magnesium). The specific calibration values for these two elements are listed in tables 1 and 2 below. The left-hand column lists the element and the figure to which the particular table relates.

TABLE 1

| B | Standard name | Int. Net. | Conc. Chem. | Conc. XRF | Abs. Dev. | Rel. Dev. | LLD (ppm) |
|---|---|---|---|---|---|---|---|
| (FIG. 3) | HP14-zero | 0.117 | 0.000 | 0.000 | −0.0002 | | 60 |
| | HP14-30 ppm | 0.123 | 0.003 | 0.003 | 0.0004 | 14.030 | 63.1 |
| | HP14-100 ppm | 0.130 | 0.010 | 0.009 | −0.0015 | −14.530 | 66.2 |
| | HP14-200 ppm | 0.144 | 0.020 | 0.019 | −0.0014 | −7.050 | 69.5 |
| | HP14-300 ppm | 0.155 | 0.030 | 0.028 | −0.0021 | −7.040 | 72.7 |
| | HP14-500 ppm | 0.180 | 0.050 | 0.050 | −0.0002 | −0.400 | 78.1 |

TABLE 2

| Mg | Standard name | Int. Net. | Conc. Chem. | Conc. XRF | Abs. Dev. | Rel. Dev. | LLD (ppm) |
|---|---|---|---|---|---|---|---|
| (FIG. 4) | HP14-zero | −0.1863 | 0.0000 | 0.0000 | 0.10 | | 0.4 |
| | HP14-10 ppm | 0.3898 | 0.0010 | 0.0006 | −4.0 | | 0.8 |
| | HP14-30 ppm | 0.6725 | 0.0030 | 0.0019 | −11.00 | −36.72 | 1.8 |
| | HP14-50 ppm | 1.0040 | 0.0050 | 0.0042 | −8.10 | −16.13 | 2.7 |
| | HP14-300 ppm | 1.3524 | 0.0100 | 0.0294 | −5.60 | −1.86 | 14.6 |
| | HP14-500 ppm | 1.3866 | 0.0200 | 0.0497 | −2.70 | −0.53 | 24.3 |
| | HP14-100 ppm | 1.3957 | 0.0300 | 0.0107 | 7.00 | 7.05 | 5.1 |
| | HP14-200 ppm | 1.4438 | 0.0500 | 0.0213 | 12.50 | 6.23 | 9.8 |

The values and curves shown in tables 1 and 2 and FIGS. 3 and 4 show that the element boron, which was not detectable to date by XFA, is detectable from a lower detection limit of approx. 60 ppm with the process according to the invention and the inventive sample body. For the likewise light element magnesium, which was to date analyzable only unreliably, a detection limit of 0.4 ppm is achieved.

FIGS. 5 to 9 show examples of calibration curves for heavier elements (heavy metals) titanium (Ti), manganese (Mn), iron (Fe), nickel (Ni) and tin (Sn) in rising sequence of their position in the periodic table. In tables 3 to 7 which follow, the specific analysis values are likewise listed therefor. For the lower detection limit, ppm values of 0.8 to 1.7 are achieved, which are thus 10%, i.e. significantly below the existing detection limit specified in the prior art.

TABLE 3

| Ti | Standard name | Int. Net. | Conc. Chem. | Conc. XRF | Abs. Dev. | Rel. Dev. | LLD (ppm) |
|---|---|---|---|---|---|---|---|
| (FIG. 5) | HP14-zero | 0.151 | 0.0000 | 0.0005 | 4.80 | | 0.8 |
| | HP14-10 ppm | 0.433 | 0.0010 | 0.0014 | 3.90 | | 0.8 |
| | HP14-30 ppm | 0.706 | 0.0030 | 0.0025 | −4.90 | −16.47 | 0.9 |
| | HP14-50 ppm | 1.073 | 0.0050 | 0.0042 | −8.10 | −16.23 | 1 |
| | HP14-100 ppm | 2.018 | 0.0100 | 0.0097 | −2.90 | −2.87 | 1.2 |
| | HP14-200 ppm | 3.002 | 0.0200 | 0.0200 | −0.40 | −0.22 | 1.7 |
| | HP14-300 ppm | 3.649 | 0.0300 | 0.0310 | 9.60 | 3.21 | 2.2 |
| | HP14-500 ppm | 4.072 | 0.0500 | 0.0495 | −4.60 | −0.92 | 3.1 |

TABLE 4

| Mn | Standard name | Int. Net. | Conc. Chem. | Conc. XRF | Abs. Dev. | Rel. Dev. | LLD (ppm) |
|---|---|---|---|---|---|---|---|
| (FIG. 6) | HP14-zero | 0.2931 | 0.0000 | 0.0000 | −0.1 | | 1.2 |
| | HP14-10 ppm | 0.6046 | 0.0010 | 0.0008 | −2.1 | | 1.2 |
| | HP14-30 ppm | 1.1590 | 0.0030 | 0.0023 | −6.8 | −22.51 | 1.3 |
| | HP14-50 ppm | 1.7251 | 0.0050 | 0.0040 | −9.8 | −19.52 | 1.3 |
| | HP14-100 ppm | 3.3615 | 0.0100 | 0.0095 | −4.7 | −4.66 | 1.5 |
| | HP14-200 ppm | 5.7046 | 0.0200 | 0.0201 | 0.7 | 0.36 | 1.7 |
| | HP14-300 ppm | 7.5155 | 0.0300 | 0.0311 | 11.3 | 3.76 | 2 |
| | HP14-500 ppm | 9.2598 | 0.0500 | 0.0495 | −5.1 | −1.02 | 2.5 |

TABLE 5

| Fe | Standard name | Int. Net. | Conc. Chem. | Conc. XRF | Abs. Dev. | Rel. Dev. | LLD (ppm) |
|---|---|---|---|---|---|---|---|
| (FIG. 7) | HP14-zero | 0.8052 | 0.0000 | 0.0000 | 0 | | 1.7 |
| | HP14-10 ppm | 0.9859 | 0.0010 | 0.0011 | 1 | | 1.7 |
| | HP14-30 ppm | 1.2319 | 0.0030 | 0.0027 | −2.6 | −8.74 | 1.8 |
| | HP14-50 ppm | 1.4421 | 0.0050 | 0.0043 | −7.5 | −14.961 | 1.8 |
| | HP14-100 ppm | 2.1989 | 0.0100 | 0.0099 | −0.9 | −0.881 | 1.9 |
| | HP14-200 ppm | 3.2578 | 0.0200 | 0.0200 | 0.3 | 0.152 | 2.2 |
| | HP14-300 ppm | 4.2047 | 0.0300 | 0.0313 | 12.7 | 4.225 | 2.4 |
| | HP14-500 ppm | 5.143 | 0.0500 | 0.0493 | −7 | −1.39 | 2.8 |

TABLE 6

| Ni | Standard name | Int. Net. | Conc. Chem. | Conc. XRF | Abs. Dev. | Rel. Dev. | LLD (ppm) |
|---|---|---|---|---|---|---|---|
| (FIG. 8) | HP14-zero | 0.0343 | 0.0000 | 0.0004 | 4.20 | | 1.7 |
| | HP14-10 ppm | 0.1640 | 0.0010 | 0.0013 | 3.30 | | 1.7 |
| | HP14-30 ppm | 0.3629 | 0.0030 | 0.0028 | −2.30 | −7.57 | 1.8 |
| | HP14-50 ppm | 0.5687 | 0.0050 | 0.0043 | −6.60 | −13.17 | 1.8 |
| | HP14-100 ppm | 1.2304 | 0.0100 | 0.0097 | −2.80 | −2.81 | 2 |
| | HP14-200 ppm | 2.2308 | 0.0200 | 0.0194 | −5.70 | −2.83 | 2.2 |
| | HP14-300 ppm | 3.2471 | 0.0300 | 0.0311 | 10.60 | 3.53 | 2.4 |
| | HP14-500 ppm | 4.3909 | 0.0500 | 0.0497 | −3.40 | −0.68 | 2.9 |

TABLE 7

| Sn | Standard name | Int. Net. | Conc. Chem. | Conc. XRF | Abs. Dev. | Rel. Dev. | LLD (ppm) |
|---|---|---|---|---|---|---|---|
| (FIG. 9) | HP14-zero | −0.0094 | 0.0000 | −0.0001 | −0.70 | | 1.7 |
| | HP14-10 ppm | 0.0946 | 0.0010 | 0.0012 | 1.50 | | 1.8 |
| | HP14-30 ppm | 0.175 | 0.0030 | 0.0024 | −5.90 | −19.57 | 2.1 |
| | HP14-50 ppm | 0.2582 | 0.0050 | 0.0040 | −9.90 | −19.86 | 2.4 |
| | HP14-100 ppm | 0.5414 | 0.0100 | 0.0108 | 7.90 | 7.90 | 3.1 |
| | HP14-200 ppm | 0.7065 | 0.0200 | 0.0204 | 3.80 | 1.92 | 4.6 |
| | HP14-300 ppm | 0.7776 | 0.0300 | 0.0294 | −6.20 | −2.06 | 6 |
| | HP14-500 ppm | 0.9009 | 0.0500 | 0.0501 | 1.40 | 0.28 | 8.7 |

Table 8 below shows the reproducibility of the process according to the invention with an inventive sample body. The sample bodies used were likewise produced from four grams of boehmite (Al(OH)O), which were processed to a pressing of diameter 40 mm. Five times 150 mg of an oil sample were applied to each of the sample bodies described and distributed homogeneously on the surface. Once the oil had been sucked away from the sample bodies, each sample body was analyzed once by means of X-ray fluorescence under vacuum, and each analysis was effected for the same selection of elements of the periodic table. The following abbreviations are used:

Mw mean ppm parts per million

StD abs. absolute standard deviation

StD rel. relative standard deviation

TABLE 8

| Sample | | Na | Si | P | S | Ca | Ti | V | Cr | Mn | Fe | Ni | Cu | Zn | Mo | Ba |
|---|---|---|---|---|---|---|---|---|---|---|---|---|---|---|---|---|
| 1 | ppm | 289 | 138 | 119 | 5681 | 260 | 198 | 198 | 162 | 153 | 180 | 111 | 93 | 90 | 29 | 206 |
| 2 | ppm | 284 | 140 | 113 | 5506 | 262 | 196 | 204 | 163 | 163 | 188 | 113 | 91 | 98 | 32 | 211 |
| 3 | ppm | 297 | 136 | 117 | 5697 | 271 | 198 | 200 | 160 | 160 | 188 | 118 | 93 | 98 | 31 | 215 |
| 4 | ppm | 285 | 135 | 112 | 5542 | 277 | 197 | 195 | 161 | 155 | 187 | 115 | 85 | 96 | 29 | 208 |
| 5 | ppm | 291 | 141 | 117 | 5412 | 259 | 190 | 197 | 158 | 155 | 182 | 115 | 89 | 96 | 28 | 207 |
| Mw | ppm | 289 | 138 | 116 | 5568 | 266 | 196 | 199 | 161 | 157 | 185 | 114 | 90 | 96 | 30 | 209 |
| StD abs. | ppm | 5.2 | 2.5 | 3.0 | 120.7 | 7.9 | 3.3 | 3.4 | 1.9 | 4.1 | 3.7 | 2.6 | 3.3 | 3.3 | 1.6 | 3.6 |
| StD rel. | % | 1.8 | 1.8 | 2.6 | 2.2 | 3.0 | 1.7 | 1.7 | 1.2 | 2.6 | 2.0 | 2.3 | 3.7 | 3.4 | 5.5 | 1.7 |

The analyses of the five sample preparations show relative standard deviations between 1.7 and 5.5%. Molybdenum (Mo) shows the highest deviation with 5.5%. This is to the particularly high penetration depth of this element and the relatively low irradiated and hence analyzable layer thickness.

LIST OF REFERENCE NUMERALS

| 1 | Rigid sample body |
| 1' | Part of the sample body impregnated by adsorbed and absorbed substance (3) |
| 2 | Analysis surface |
| 3 | Liquid or pasty substance (substance for analysis) |
| Arrow | Application path of the substance for analysis |
| 3' | Substance as an overlying film (substance film) |
| 4 | Suspended element particle in the substance to be analyzed |
| 5 | Pipette |

The invention claimed is:

1. An analysis process for analyzing liquid or pasty substances not consisting exclusively of volatile constituents, comprising:
   1) applying the substance to be analyzed to a rigid sample body with at least one flat and smooth analysis surface, said rigid sample body comprised of an absorptive material,
   2) the sample body adsorbing and absorbing the substance, and
   3) analyzing the substance by X-ray fluorescence analysis, wherein the sample body is a pressing composed of granules and comprising at least one of the following substances: a clay mineral; boehmite; apatite; tricalcium phosphate; or cellulose.

2. The analysis process as claimed in claim 1, wherein the X-ray fluorescence analysis is a wavelength-dispersive or energy-dispersive X-ray fluorescence analysis.

3. The analysis process as claimed in claim 1, wherein the sample body used in step 1 binds and/or retains the substance in step 2 such that it remains bound or retained even under vacuum.

4. The analysis process as claimed in claim 1, which comprises, as a further step between step 2 and step 3:
   removing a substance film on element particles on the analysis surface of the sample body via a heat treatment.

5. The analysis process as claimed in claim 1, wherein the sample body comprises activated carbon.

6. A sample body for the analysis of liquid or pasty substances by X-ray fluorescence analysis as claimed in claim 1, comprising at least one flat and smooth analysis surface, wherein said sample body consists of absorptive, rigid material, the sample body being a pressing composed of granules and the sample body consisting of one of the following substances: a clay mineral; boehmite; apatite; and tricalcium phosphate.

7. The sample body as claimed in claim 6, wherein the absorptive, rigid material can retain and/or bind liquid or pasty substances sufficiently firmly that they remain retained or bound even under vacuum.

8. The sample body as claimed in claim 6, wherein the liquid or pasty substance does not consist exclusively of volatile constituents.

9. The sample body as claimed in claim 6, wherein the clay mineral is a clay mineral granule.

10. The sample body as claimed in claim 6, wherein the boehmite is a boehmite granule.

11. The analysis process as claimed in claim 1, wherein the rigid sample body consists of absorptive material.

12. The analysis process as claimed in claim 1, wherein the clay mineral is a clay mineral granule.

13. The analysis process as claimed in claim 1, wherein the boehmite is a boehmite granule.

14. The analysis process as claimed in claim 1, wherein the substance to be analyzed is not subjected to a drying step before being analyzed in step 3.

15. A process for preparing liquid or pasty substances not consisting exclusively of volatile constituents for X-ray fluorescence analysis, comprising the following steps:
   1) applying the substance to be analyzed to a rigid sample body with at least one flat and smooth analysis surface, said rigid sample body comprised of an absorptive material, and
   2) the sample body adsorbing and absorbing the substance, wherein the sample body is a pressing composed of granules and consisting of one of the following substances: a clay mineral; boehmite; apatite; and tricalcium phosphate.

16. The process as claimed in claim 15, wherein the sample body used in step 1 binds and/or retains the substance in step 2 such that it remains bound or retained even under vacuum.

17. The process as claimed in claim 15, which comprises, as a further step:
   3) removing a substance film on element particles on the analysis surface of the sample body via a heat treatment.

18. The process as claimed in claim 15, wherein the rigid sample body consists of absorptive material.

19. The process as claimed in claim 15, wherein the clay mineral is a clay mineral granule.

20. The process as claimed in claim 15, wherein the boehmite is a boehmite granule.

21. The process as claimed in claim 15, wherein the substance to be analyzed is not subjected to a drying step.

22. An analysis process for analyzing liquid or pasty substances not consisting exclusively of volatile constituents, comprising:

1) applying the substance to be analyzed to a rigid sample body with at least one flat and smooth analysis surface, said rigid sample body formed of an absorptive material, and 2) analyzing the substance by X-ray fluorescence analysis, wherein the sample body is a pressed composite of granules of at least one of a clay mineral or a boehmite.

23. The analysis process as claimed in claim 22, wherein the substance to be analyzed is not subjected to a drying step before being analyzed in step 2.

* * * * *